United States Patent [19]

Blake et al.

[11] Patent Number: 5,445,632

[45] Date of Patent: Aug. 29, 1995

[54] ARTERIAL CUFF GRAFT EVERSION INSTRUMENT

[75] Inventors: Kenneth R. Blake, Brooklyn Park, Minn.; Kazi Mobin-Uddin, Worthington, Ohio

[73] Assignee: Scanlan International, Inc., St. Paul, Minn.

[21] Appl. No.: 133,608

[22] Filed: Oct. 8, 1993

[51] Int. Cl.6 .............................................. A61B 19/00
[52] U.S. Cl. ........................................................ 606/1
[58] Field of Search ......................... 294/3.6, 19.1, 26; 606/1, 106, 108, 161, 159, 205–207

[56] References Cited

U.S. PATENT DOCUMENTS

| | | | |
|---|---|---|---|
| 2,597,400 | 5/1952 | Stogsdill et al. | 294/26 |
| 2,604,350 | 7/1952 | Taylor | 294/26 |
| 2,610,884 | 9/1952 | Enderle et al. | 294/26 |
| 3,162,475 | 12/1964 | Van Allen | 294/26 |
| 3,242,540 | 3/1966 | Mitchell | 294/26 |
| 4,265,231 | 5/1981 | Scheller et al. | 606/80 |
| 4,955,647 | 9/1990 | Alfredson | 294/26 |
| 5,282,796 | 2/1994 | Knoepfler | 606/106 |

FOREIGN PATENT DOCUMENTS

| | | | |
|---|---|---|---|
| 2239786 | 7/1991 | United Kingdom | 294/26 |
| 1049047 | 10/1983 | U.S.S.R. | 606/1 |

*Primary Examiner*—Stephen C. Pellegrino
*Assistant Examiner*—Glenn Dawson
*Attorney, Agent, or Firm*—Faegre & Benson

[57] ABSTRACT

An arterial cuff graft eversion instrument including a handle with a longitudinally straight wire extending distally from the handle distal end. The wire terminates at its distal end in a "pig-tail" loop of a circular configuration. The open "pig-tail" loop allows arterial cuff graft eversion without the need of suturing the end of the graft to the instrument prior to the eversion procedure.

6 Claims, 2 Drawing Sheets

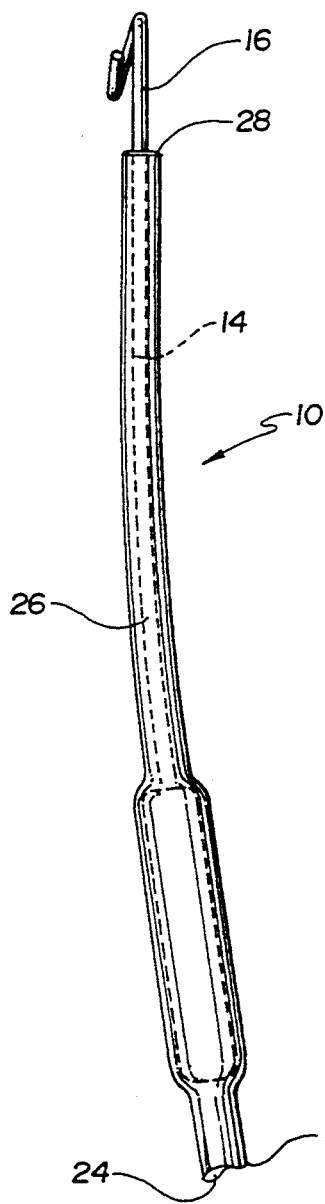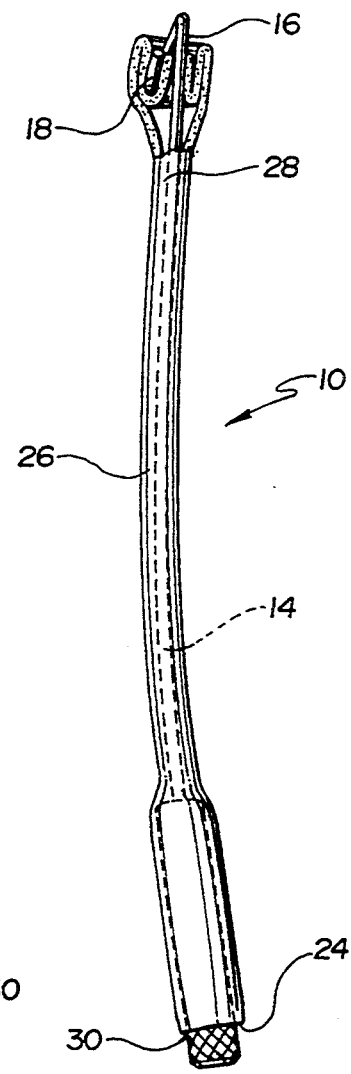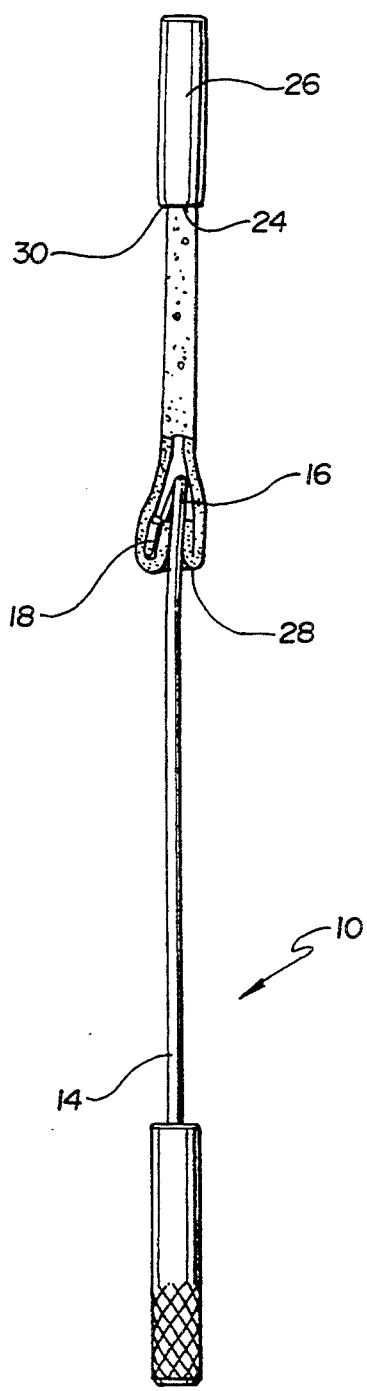

ARTERIAL CUFF GRAFT EVERSION INSTRUMENT

FIELD OF THE INVENTION

This invention relates to a method for everting an arterial cuff graft in preparation for the performance of a femoral popliteal arterial bypass, and to an arterial cuff graft eversion instrument for use in this surgical procedure.

BACKGROUND OF THE INVENTION

A common medical problem, particularly for patients advancing in age, is arthrosclerosis or hardening of the arteries. Blockages develop in the arteries and restrict circulation of blood to the limbs or organs. In the legs such blockage of circulation may result in pain in the leg while walking, which may progress to rest pain, tissue necrosis and, finally, gangrene and subsequent amputation. Correction of this condition may require surgical intervention including what is commonly known as femoral-popliteal arterial bypass surgery, whereby a new blood passageway around the area of blockage is established to improve circulation of blood to the lower extremity.

A method for this procedure utilizes an arterial cuff graft for anastomosis to the host artery junction and an artificial bypass graft, such as one made of PTFE. In preparing the arterial cuff graft, it is necessary to evert the arterial cuff graft and, following preparation of the arterial graft, return the graft to its original position.

This procedure was first described by J. Harold Harrison, M.D., W. D. Jordan, M.D., and Antonio R. Perez, M.D., in *Surgery*, Vol. 61, No. 1, pp. 26–30, January 1967. The instrument described for use in that procedure required insertion of the instrument into the graft and suturing of the graft to the distal portion of the instrument prior to retraction of the instrument for graft reversal.

Certain problems have been noted in the use of the instrument described by Harrison, et al. The Harrison instrument is cumbersome to use, because suturing of the arterial host graft to the instrument is required. Suturing may cause unnecessary damage to the graft. The use of the Harrison instrument requires highly skilled surgical technique in handling to avoid damage to the graft. The need for suturing the graft to the Harrison instrument adds to the difficultly of reverse eversion of the arterial graft cuff once surgical changes to the graft have been performed.

There has thus been a need for a carefully and uniquely designed graft eversion instrument which will adequately, yet without damage, reverse the graft.

BRIEF DESCRIPTION OF THE INVENTION

The arterial cuff graft eversion instrument of this invention comprises a handle with a proximal and a distal end, and a longitudinally straight wire extending distally from the handle distal end. The wire terminates at the distal end of the wire in a "pig-tail" single loop of a circular configuration. Having completed the formation of the loop, the free distal end of the wire terminates after slightly crossing over and overlapping the longitudinally straight portion of the wire.

The method of performing an arterial cuff graft eversion according to this invention used the instrument as described in the paragraph above. The method comprises inserting the instrument into the lumen of an arterial cuff graft and extending the instrument to the distal end of the graft;

locating the "pig-tail" loop on the lumen surface of the distal end of the graft so that the distal end of the graft is engaged between the free distal end of the wire and the straight longitudinal portion of the wire, while at the same time stabilizing the proximal portion of the graft;

slightly rotating the instrument until the distal end of the graft is engaged within the loop and then drawing the engaged distal portion of the graft inward through the lumen as the instrument is retracted proximally;

continuing to retract the instrument proximally, while drawing the proximal portion of the graft distally, thereby reversing the graft.

BRIEF DESCRIPTION OF THE DRAWINGS

FIG. 3 is a perspective view of the arterial cuff graft eversion instrument inserted into the lumen of an arterial cuff graft extending to the distal end of the graft.

FIG. 4 is a perspective view of the distal end of the graft engaged between the free distal end of the wire and the straight longitudinal portion of the wire within the loop of the wire of the wire of the arterial cuff graft eversion instrument, with the instrument retracted proximally within the cuff graft.

FIG. 5 is a perspective view of the arterial cuff graft eversion instrument retracted further proximally within the cuff graft and the proximal portion of the graft drawn distally, reversing the graft inside out.

DETAILED DESCRIPTION OF THE INVENTION

Figure 1:
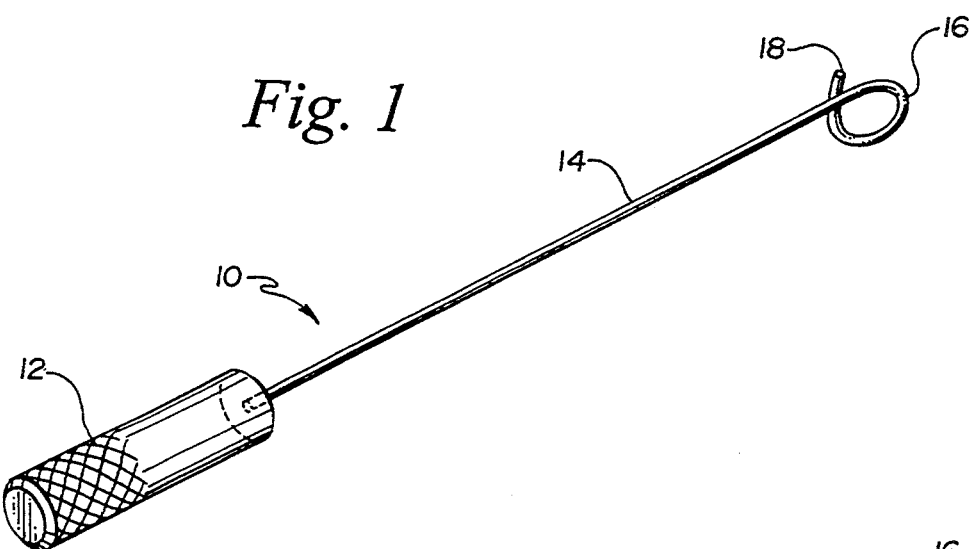
FIG. 1 is a perspective view of an arterial cuff graft eversion instrument of the present invention.

As shown in FIG. 1, the eversion instrument 10 includes a handle 12 and a longitudinally straight wire 14 extending distally therefrom terminating in a distally formed "pig-tail" loop 16 slightly overlapping the wire 14. In the eversion instrument 10 of FIG. 1, the handle 12 is a slender elongate cylinder inscribed with a knurled or similar non-slip surface to facilitate easy and secure gripping by the surgeon's gloved hand. The longitudinal axis of the wire 14 is co-axial with the longitudinal axis of the handle 12. The "pig-tail" loop 16 is of a circular configuration. Having completed the formation of the loop 16, the free distal end of the wire 18 terminates after slightly crossing over and overlapping the longitudinally straight portion of the wire 14.

Figure 2:
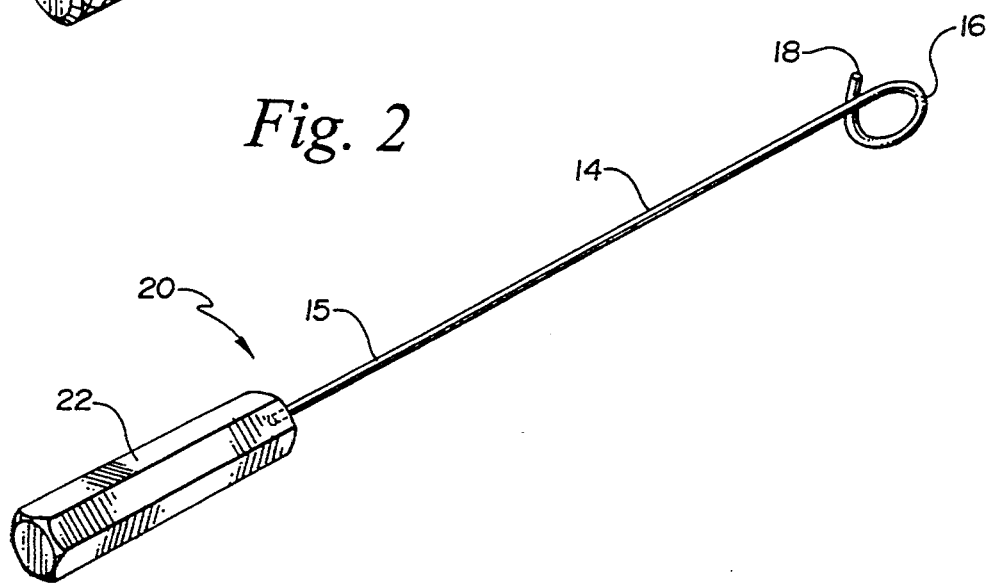
FIG. 2 is a perspective view of another arterial cuff graft eversion instrument of the present invention.

In the eversion instrument 20 shown in FIG. 2, the handle 22 is slender and elongate with a hexagonal cross-section, to provide sensitive translation of motion to the surgeon's hand and, to facilitate determining rotational position of the "pig-tail" loop 16 at the distal end of the wire 14. If desired, the handle 22 may similarly have a knurled surface.

The handle 12, 22 may be formed of metal, such as stainless steel, or molded of a synthetic resin, such as polypropylene. The eversion instrument 10, 20 can suitably be made approximately 11 cm. in overall length. The handle 12, 22 can be approximately 4 cm. in length. The wire 14 is generally a surgical grade stainless steel wire approximately 0.4 mm. in diameter. The circular "pig-tail" loop configuration 16 has a diameter of about 0.5 cm. The eversion instrument 10, 20 may be a single use instrument, if desired, to assure that the wire 14 and "pig-tail" loop 16 are in correct orientation for use.

The eversion instrument 10, 20 is simple to use. The instrument 10, 20 is inserted into the lumen 24 of the arterial cuff graft 26 and extended to the distal end of the graft 28. The "pig-tail" loop 16 is drawn to one side of the distal end of the graft 28, while the proximal portion of the graft 30 is held steady. The distal end 28 of the graft 26 is engaged between the free distal end 18 of the wire and the straight longitudinal portion of the wire 14. As the "pig-tail" loop 16 engages the distal portion of the graft 28, the instrument 10, 20 is rotated slightly between the forefingers and the thumb, causing the distal portion of the graft 28 to be drawn inward through its lumen 24. The instrument 10, 20 is drawn proximally as the proximal portion of the graft 30 is drawn distally, reversing the graft 26 for surgical intervention. The graft 26 is then removed of its intimal surface, along with any atherosclerotic evidence to assure a smooth, uniform lumen 24.

The instrument 10, 20 is once again inserted into the arterial cuff graft 26, again engaging the distal end of the graft 28, so that the graft 26 can again be reversed in the same motion as previously described.

It will be apparent to those of skill in this art, that the medical eversion instrument of this invention may suitably be used for ex vivo eversion of other body members by forming the instrument to the appropriate required dimensions and by using the instrument according to the above described procedure.

What is claimed is:

1. An arterial cuff graft eversion instrument comprising:
    a handle with a proximal and a distal end; and
    a single wire, having a longitudinally straight portion extending distally from only the handle distal end, said wire configured at a distal end of the instrument into a single loop of a circular configuration, such that a free distal end of the wire terminates immediately after slightly crossing over and overlapping the longitudinally straight portion of the wire;
    so that the instrument is adapted for performing an arterial cuff graft eversion by:
    inserting the instrument into a lumen of an arterial cuff graft and extending the instrument to a distal end of the graft;
    locating the loop on an edge of the distal end of the graft, so that the distal end of the graft is engaged between the free distal end of the wire and the straight longitudinal portion of the wire, while stabilizing a proximal portion of the graft;
    slightly rotating and retracting the instrument, until the distal end of the graft is engaged within the loop, and then drawing the engaged distal portion of the graft inward through the lumen as the instrument is retracted proximally, and;
    continuing to retract the instrument proximally, while urging a proximal portion of the graft distally, thereby reversing the graft.

2. The instrument according to claim 1, wherein the handle is a slender elongate cylinder with a non-slip surface on the proximal end thereof.

3. The instrument according to claim 1, wherein the handle is slender and elongate with a hexagonal cross-section.

4. The instrument according to claim 1, wherein the handle and the wire are constructed of stainless steel.

5. The instrument according to claim 2, wherein the instrument is about 11 cm long, the handle is about 4 cm long, and the loop has a diameter of about 0.5 cm.

6. A method of performing an arterial cuff graft eversion using the instrument according to claim 1 comprising:
    inserting the instrument into a lumen of an arterial cuff graft and extending the instrument to a distal end of the graft;
    locating the loop on an edge of the distal end of the graft so that the distal end of the graft is engaged between the free distal end of the wire and the straight longitudinal portion of the wire, while stabilizing a proximal portion of the graft;
    slightly rotating and retracting the instrument, until the distal end of the graft is engaged within the loop, and then drawing the distal end of the graft inward through the lumen as the instrument is retracted proximally;
    continuing to retract the instrument proximally, while urging a proximal portion of the graft distally, thereby reversing the graft.

* * * * *